United States Patent
Ottaway et al.

(10) Patent No.: US 6,451,735 B1
(45) Date of Patent: Sep. 17, 2002

(54) GLYPHOSATE FORMULATION

(75) Inventors: Alan Victor Ottaway; Carl Andrew Formstone, both of Maidstone; Derek John Hopkins; Michael John Bean, both of Bracknell, all of (GB)

(73) Assignee: Syngenta Limited (GB)

( * ) Notice: Subject to any disclaimer, the term of this patent is extended or adjusted under 35 U.S.C. 154(b) by 0 days.

(21) Appl. No.: 09/605,069

(22) Filed: Jun. 28, 2000

Related U.S. Application Data

(63) Continuation of application No. PCT/GB99/02726, filed on Aug. 18, 1999.

(30) Foreign Application Priority Data

Sep. 10, 1998 (GB) .............................................. 9819693

(51) Int. Cl.$^7$ ........................ A01N 25/30; A01N 57/02
(52) U.S. Cl. ...................................... 504/206; 504/365
(58) Field of Search ................................ 504/206, 365

(56) References Cited

U.S. PATENT DOCUMENTS

| | | | |
|---|---|---|---|
| 3,799,758 A | 3/1974 | Franz | |
| 3,853,530 A | 12/1974 | Franz | |
| 3,977,860 A | 8/1976 | Franz | |
| 4,140,513 A | 2/1979 | Prill | |
| 4,315,765 A | 2/1982 | Large | |
| 4,405,531 A | 9/1983 | Franz | |
| 4,481,026 A | 11/1984 | Prisbylla | |
| 4,507,250 A | 3/1985 | Bakel | |
| 5,652,197 A | 7/1997 | Claude et al. | |
| 5,668,085 A | 9/1997 | Forbes et al. | |
| 5,683,958 A | 11/1997 | Berger et al. | |
| 5,703,015 A | 12/1997 | Berger et al. | |
| 5,750,468 A | 5/1998 | Wright et al. | |
| 5,958,104 A * | 9/1999 | Nonomura et al. | ............. 71/11 |
| 6,040,272 A * | 3/2000 | Riego et al. | ................. 504/206 |
| 6,063,733 A | 5/2000 | Berger et al. | |
| 6,117,820 A * | 9/2000 | Cutler et al. | ................. 504/206 |
| 6,121,199 A * | 9/2000 | Berger et al. | ............... 504/206 |
| 6,121,200 A | 9/2000 | Berger et al. | |
| 6,277,788 B1 | 8/2001 | Wright | |
| 6,365,551 B1 | 4/2002 | Wright et al. | |
| 2001/0019997 A1 | 9/2001 | Wright | |

FOREIGN PATENT DOCUMENTS

| | | |
|---|---|---|
| EP | 0 290 416 B1 | 6/1993 |
| EP | 0 364 202 B1 | 8/1995 |
| EP | 0 472 310 B1 | 12/1996 |
| GB | 1588079 | 4/1981 |
| WO | 97/32476 | 9/1997 |
| WO | 98/15181 | 4/1998 |
| WO | WO98/33384 | 8/1998 |
| WO | WO98/33385 | 8/1998 |
| WO | WO00/15037 | 3/2000 |
| WO | 00/30451 | 6/2000 |
| WO | WO01/89302 A2 | 11/2001 |

OTHER PUBLICATIONS

Hughes, Harold A. Fundamentals of Machine Operation. John Deere. p. 129–131. 1976.*

Franz et al, Glyphosate: A Unique Global Herbicide, American Chemical Society, p. 39 (1997).

* cited by examiner

*Primary Examiner*—S. Mark Clardy
(74) *Attorney, Agent, or Firm*—Hale and Dorr LLP

(57) ABSTRACT

A storage-stable high-strength aqueous glyphosate concentrate, preferably containing greater than 400 g/l glyphosate expressed as acid, comprises the potassium salt of glyphosate, an alkylglycoside surfactant and an alkoxylated alkylamine surfactant at a preferred total concentration of alkylglycoside and alkoxylated alkylamine from about 160 to 300 g/l and at a preferred ratio of alkylglycoside to alkoxylated alkylamine of from about 1 part by weight of alkylglycoside per 1 part by weight of alkoxylated alkyl amine to about 5 parts by weight of alkylglycoside per 1 part by weight of alkoxylated alkylamine.

28 Claims, No Drawings

GLYPHOSATE FORMULATION

RELATED APPLICATIONS

This application is a continuation of PCT/GB99/02726 filed Aug. 18, 1999, which claims priority to United Kingdom Application No. 9819693.4 filed Sep. 10, 1998.

This invention relates to a glyphosate formulation and in particular to a high-strength aqueous concentrate formulation of glyphosate.

N-phosphonomethylglycine (referred to herein by the common name glyphosate) is a well-known herbicide which is generally used in the form of its salts. Glyphosate may be formulated in a wide variety of liquid and solid compositions designed to cover a range of commercial applications. This invention concerns liquid concentrate formulations which are designed to be diluted prior to use. Many such liquid concentrates are sold commercially but there are strong commercial and environmental reasons for seeking to increase the concentration of glyphosate in the aqueous formulation beyond that which is commonly available. It is readily apparent that a high-strength aqueous concentrate formulation provides a given dose of glyphosate in a smaller liquid volume, resulting in significant advantages in terms of reduced transport, storage and handling costs and reduced and more convenient container disposal.

It is well understood that in commercial practice it is necessary to enhance the activity of glyphosate by the use of one or more surfactants and many effective individual surfactants or mixed surfactant systems have been published in the literature. It is possible to add a desired surfactant system separately into a tank mix at the same time that the aqueous glyphosate concentrate is diluted, and the surfactant system may thus be omitted from the concentrate and added separately at the tank mix stage. Clearly however the addition of a separate component at the tank mix stage constitutes and additional step prior to spraying the herbicide and requires the user to undertake accurate measurement of mixing volumes to ensure the correct proportions in the final product. There is a need therefore for high-strength glyphosate concentrates in which an effective proportion of a surfactant system is "built-in" to the composition. It is this factor which has hitherto limited the practical realisation of effective high-strength glyphosate concentrates containing surfactant, since such concentrates have to be physically stable over extended storage at the possible extremes of ambient temperatures likely to be encountered in commercial usage. It is exceptionally difficult to "build-in" effective levels of conventional surfactant systems to high-strength formulations, for example formulations containing glyphosate salts at a concentration of greater than 400 or 450 g/l based on glyphosate acid.

A still further problem which is encountered in highly concentrated systems incorporating both a salt of glyphosate and a surfactant system is that of viscosity. The advantages of having a low-volume, high-strength composition will to a greater or lesser extent be negated in practice if the composition is too viscous to be poured conveniently from the container or is too viscous for residues to be washed rapidly from the container. This is of particular importance if the product is to be supplied in bulk for large-scale users.

Many salts of glyphosate are disclosed in the literature, but extensive commercial use has only been made of liquid concentrates containing the trimethylsulphonium salt and the isopropylamine salt. The ammonium or sodium salt is used in some solid formulations. We have now found that the potassium salt of glyphosate is especially well suited to the provision of a high-strength aqueous concentrate of glyphosate since it is readily soluble in water to form relatively high density solutions (about 1.45 g/cc). Extensive investigation of conventional surfactant systems has shown however that it is exceptionally difficult to build-in effective levels of surfactant to provide a physically stable high-strength composition containing salts of glyphosate such as the potassium salt.

According to the present invention there is provided a high-strength aqueous glyphosate concentrate comprising the potassium salt of glyphosate, an alkylglycoside surfactant and an alkoxylated alkylamine surfactant.

As used herein, the term "high-strength" aqueous glyphosate concentrate indicates a concentrate in which the glyphosate concentration is greater than 400 g/l and more particularly greater than 440 g/l based on glyphosate acid content. It should be noted that, unless otherwise stated, all concentrations of glyphosate are given herein in terms of the percentage by weight of glyphosate acid even when the glyphosate is present as a salt. In general a practical upper limit of the glyphosate concentration will be determined by viscosity considerations. As discussed below, viscosity modifying agents may be required if the concentration is much in excess of 500 g/l, whilst formulations in which the concentration is in excess of 550 g/l will tend to be too viscous for effective commercial usage using conventional equipment. Compositions of the present invention wherein the glyphosate content is from about 440 gl/l to about 540 g/l are especially effective.

Preferably the total content of the alkylglycoside and alkoxylated alkylamine surfactant system in the aqueous concentrate is from about 160 to 300 g/l, for example from about 200 to 270 g/l. Whilst additional surfactants other than the alkylglycoside and the alkoxylated alkylamine may be used if desired, the presence of such additional surfactants may adversely affect the formulation stability when used at the upper limit of concentration of alkylglycoside and alkoxylated alkylamine.

The ratio of alkylglycoside to alkoxylated alkylamine in the surfactant system is preferably from about 1 part by weight of alkylglycoside per 1 part by weight of alkoxylated alkylamine to about 5 parts by weight of alkylglycoside per 1 part by weight of alkoxylated alkylamine. An especially preferred ratio is from about 1.5 or more preferably 2 parts by weight of alkylglycoside per 1 part by weight of alkoxylated alkylamine to about 4 parts by weight of alkylglycoside per 1 part by weight of alkoxylated alkylamine.

Whist the scope of the present invention is not to be taken as being limited by any one particular theory and whilst the mode of action of surfactants is extremely complex, it is believed that the alkylglycoside and the alkoxylated alkylamine function by different general mechanisms and are able to work together to provide the maximum adjuvant effect together with the optimum capacity to be built-in to the high-strength formulation without loss of physical stability of the formulation. Specifically, the alkylglycoside is believed to operate essentially passively, being located largely on the leaf surface and moderating the physical properties of the spray solution as it dries to ensure effective uptake. One phenomenon which is believed to be a consequence of this mode of action is that if the loading of alkylglycoside is increased past a particular optimum range, the enhancement of activity is no longer proportional to the loading of alkylglycoside. Addition of further alkylglycoside then has relatively little effect. Alkoxylated alkylamines on the other hand are believed to operate by a more active mechanism in which the alkoxylated alkylamine penetrates the leaf cuticle and provides enhancement of biological activity by facilitating penetration of the active ingredient into the plant system.

Thus whilst it would be possible to incorporate a relatively high loading of alkylglycoside into a high-strength potassium glyphosate formulation, the enhancement of biological activity would tend to be less than optimum and in addition the viscosity of the resultant solution would tend to be undesirably high. Alkoxylated alkylamines on the other hand have a relatively low compatibility threshold in high-strength glyphosate concentrates. We have found however that the claimed glyphosate composition combines the high-strength capability of the potassium salt with the optimum "passive" enhancement of activity by the alkylglycoside and the "penetrant" enhancement provided by relatively low levels of alkoxylated alkylamine which are compatible with the system as a whole. The claimed high-strength glyphosate composition thus contains a much higher loading of total surfactant than has hitherto proved possible for such high-strength compositions and as a result exhibits an excellent biological activity, comparable with many commercially formulations of much lower glyphosate strength. Appropriate selection of the alkoxylated alkylamine, as discussed in greater detail below, additionally ensures an operating viscosity of the concentrate which is well within acceptable commercial limits.

The alkylglycoside for use in the present invention may be obtained by the reaction of alkanols with glucose or other mono- or di- or polysaccharides. As used herein the term "alkylglycoside" includes an alkylmonoglycoside and an alkylpolyglycoside. Preferred alkylglycosides for use in the present invention are alkylglucosides obtained by the reaction of glucose with a straight or branched chain alkanol or mixture of alkanols, for example a mixture of alkanols containing 7 to 18, preferably 7 to 16 carbon atoms for example 8 to 10 carbon atoms or a single branched chain alcohol containing 8 carbon atoms. The number of glycose groups per alkyl group in the molecule may vary and alkyl mono- or di- or polyglucose or saccharide derivatives are possible. Commercial alkylpolyglucosides usually contain a mixture of derivatives having an average number of glycose groups per alkyl group. Thus alkylglycosides have the general formula (I)

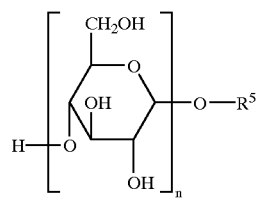

(I)

wherein n is the degree of polymerisation and is typically within the range from 1 to 3, for example from 1 to 2, and $R^5$ is a branched or straight chain alkyl group having from 4 to 18 carbon atoms or a mixture of alkyl groups having an average value within the given range. Typical of alkylglycosides is the product commercially available under the trade names AL2042 (Imperial Chemical Industries PLC) and AGRIMUL PG2067 (Henkel Corp) wherein n is an average of 1.7 and $R^5$ is a mixture of octyl (45%) and decyl (55%), the product commercially available under the trade name AGRIMUL PG2069 (Henkel Corp) wherein n is an average of 1.6 and $R^5$ is a mixture of nonyl (20%), decyl (40%) and undecyl (40%) and 2-ethyl-1-hexylglycoside wherein $R^5$ is 2-ethyl-1-hexyl and is derived from a single branched alcohol (2-ethyl-1-hexanol) and the degree of polymerisation (n) is from 1 to 2, for example from 1.5 to 1.9, such as about 1.75.

Suitably the alkyl group in the alkoxylated alkylamine contains from 8 to 22 carbon atoms (or an average of from 8 to 22 carbon atoms if a mixture of alkyl groups is present) and may be linear or branched. It is especially preferred that the alkyl group contains from 10 to 20 carbon atoms. Specific examples of preferred alkoxylated alkylamines are alkoxylated derivatives of cocamine, tallowamine, oleylamne and stearylamine. Typically such alkoxylated alkylamine surfactants are available with an average degree of alkoxylation of from 1 to about 15. Suitable alkoxy groups include ethoxy, propoxy or a mixture thereof. Ethoxy is particularly preferred. Thus the alkoxylated alkylamine is suitably an ethoxylated or propoxylated or mixed ethoxylated and propoxylated C8 to 22 alkylamine having a degree of alkoxylation of from 1 to about 15.

Whilst it is possible to use an alkoxylated alkylamine in the composition of the present invention having an average degree of alkoxylation (or more specifically ethoxylation) in the commercially available range, for example from 1 to about 15, we have found that ethoxylated alkylamines having a high degree of ethoxylation are less compatible with the high-strength composition than are those having a lower degree of ethoxylation. Thus it is preferred that the average degree of alkoxylation (or more specifically ethoxylation) is from 2 to 12. We have also found however that alkoxylated alkylamines having a low degree of alkoxylation (or more specifically ethoxylation) of about two tend to increase the viscosity of the composition. Thus it is especially preferred that the average degree of alkoxylation (or more specifically ethoxylation) is from 4 to 12. An example of a particularly suitable alkoxylated alkylamine is an ethoxylated alkylamine having an average degree of ethoxylation of about 5, for example an ethoxylated cocoamine having an average degree of ethoxylation of about 5.

If the viscosity of the composition is high, for example if the concentration of the potassium glyphosate is towards the upper limit of the range, it may be appropriate to add a viscosity modifying agent. Suitable viscosity modifying agents include propylene glycol. As is conventional practice with formulations containing an alkylglycoside, an antifoam may be added. Numerous antifoams are known in the art and commercially available antifoams operate at very low concentrations (for example less than 5 g/l) and hence do not have a major impact on the loading of the composition.

Other conventional additives such as humectants, activity enhancers (such as inorganic ammonium salts), anti-freeze agents, wetters, or other additional surfactants may be added if desired, but it is generally preferred not to add to the loading of the composition by the addition of such materials, particularly if they are present in substantial quantities. Similarly, additional water-soluble herbicides or other agro-chemicals such as fungicides and insecticides may be incorporated if desired, but the present invention is primarily concerned with compositions in which the only active agrochemical ingredient is glyphosate.

When diluted for use, compositions of the present invention are active against a broad range of weed species including monocotyledonous and dicotyledonous species. The compositions are suitably applied directly to unwanted plants (post-emergence application).

Thus according to a further aspect of the present invention there is provided a process of severely damaging or killing unwanted plants which comprises diluting a concentrated composition of the present invention and applying to the plants a herbicidally effective amount of a said diluted composition.

The rate of application of the composition of the invention will depend on a number of factors including, for example, the identity of the plants whose growth is to be inhibited and whether the compound is to be applied for foliage or root uptake. As a general guide, however, an application rate of from 0.001 to 20 kilograms per hectare is suitable while from 0.025 to 10 kilograms per hectare may be preferred.

The invention is illustrated by the following Examples in which all parts and percentages are by weight unless otherwise stated.

EXAMPLES 1 TO 15

In the following Examples, compositions were prepared by dissolving glyphosate acid (referred to in the tables as PMG acid) in sufficient of a 50% by weight potassium hydroxide solution to neutralise the acid and form the potassium salt. Thus for example when the concentration of PMG acid was 450 g/l, the corresponding proportion of 50% potassium hydroxide solution was 334 g/l. The remaining components were added in the indicated proportions (g/l) and water was added proportionately to make up the liter.

All formulations were evaluated for physical stability on storage at 54° C. for 4 weeks and at −10° C. for two weeks. Formulations given stability code "A" in Tables 1 to 4 below remained physically stable after this test. Formulations given stability code "B" remained physically stable at room temperature but failed to remain stable during the 4 week test at 54° C., showing evidence of phase separation.

The alkylglycoside used (APG) in Tables 1 to 4 was AGRIMUL PG2067 whose composition has been given earlier.

ETHOMEEN C15 (ETHOMEEN is a trademark of Akzo Nobel) is an ethoxylated cocoamine having an average degree of ethoxylation of 5.

ETHOMEEN C12 is an ethoxylated cocoamine having an average degree of ethoxylation of 2.

ETHOMEEN T15 is an ethoxylated tallowamine having an average degree of ethoxylation of 5.

ETHOMEEN T25 is an ethoxylated tallowamine having an average degree of ethoxylation of 15.

ETHOMEEN S22 is an ethoxylated soyamine having an average degree of ethoxylation of 12.

TABLE 1

| | Example No. | | | | | | |
|---|---|---|---|---|---|---|---|
| | 1 | 2 | 3 | 4 | 5 | 6 | 7 |
| PMG - acid (g/l) | 540 | 500 | 450 | 450 | 450 | 450 | 450 |
| Alkylglucoside (g/l) | 214 | 172.2 | 229 | 197 | 161 | 160 | 157 |
| "Ethomeen" C15 (g/l) | 50 | 46.3 | 50 | 50 | 75 | 75 | 100 |
| Antifoam (g/l) | 0.7 | 1.3 | 0.7 | 0.7 | 0.7 | 0.7 | 0.7 |
| Stability code | A | A | A | A | A | A | A |

TABLE 2

| Example No | 8 | 9 | 10 | 11 |
|---|---|---|---|---|
| PMG — acid (g/l) | 540 | 450 | 450 | 450 |
| Alkylglucoside (g/l) | 186 | 197 | 161 | 126 |
| "Ethomeen" T15 (g/l) | 50 | 50 | 75 | 100 |
| Antifoam (g/l) | 0.7 | 0.7 | 0.7 | 0.7 |
| Stability code | A | A | A | A |

TABLE 3

| Example No | 12 | Example No | 13 |
|---|---|---|---|
| PMG — acid (g/l) | 450 | PMG — acid (g/l) | 450 |
| Alkylglucoside (g/l) | 197 | Alkylglucoside (g/l) | 197 |
| "Ethomeen" C15 (g/l) | 10 | "Ethomeen" C15 (g/l) | 10 |
| "Ethomeen" S22 (g/l) | 40 | "Ethomeen" T25 (g/l) | 40 |
| Antifoam (g/l) | 0.7 | Antifoam (g/l) | 0.7 |
| Stability code | A | Stability code | B |

TABLE 4

| Example No | 14 | Example No | 15 |
|---|---|---|---|
| PMG — acid (g/l) | 450 | PMG — acid (g/l) | 540 |
| Alkylglucoside (g/l) | 229 | Alkylglucoside (g/l) | 186 |
| "Ethomeen" C12 (g/l) | 50 | "Ethomeen" C15 (g/l) | 50 |
| Antifoam (g/l) | 0.7 | Antifoam (g/l) | 1.3 |
| | | Propylene glycol | 25 |
| Stability code | A | Stability code | A |

Examples 12 and 13 illustrate that physical stability of the formulation is satisfactory given an average ethylene oxide content of the ethoxylated alkylamine of 10.6 (10 parts "Ethomeen" C15 and 40 parts "Ethomeen" S22), but has less than optimum physical stability when the average ethylene oxide content of the ethoxylated alkylamine is 13 (10 parts "Ethomeen" C15 and 40 parts "Ethomeen" T25).

In Example 15 the viscosity of the formulation containing 540 g/l of glyphosate acid was reduced by the addition of propylene glycol.

EXAMPLES 16 AND 17

The procedure of Examples 1 to 15 was followed except that the alkylglycoside used was 2-ethyl-l-hexylglycoside having a degree of polymerisation of about 1.75. Formulations having the compositions shown in Table 5 were prepared and were found to be stable at least over the range −10° C. to 40° C.

TABLE 5

| Example No | 16 | Example No | 17 |
|---|---|---|---|
| PMG — acid (g/l) | 450 | PMG — acid (g/l) | 500 |
| 2-ethyl hexyl glucoside (g/l) | 197 | 2-ethyl-hexyl glucoside (g/l) | 172.2 |
| "Ethomeen" C15 (g/l) | 50 | "Ethomeen" C15 (g/l) | 46.3 |

What is claimed is:

1. A high strength aqueous glyphosate concentrate comprising the potassium salt of glyphosate, an alkylglycoside surfactant and an alkoxylated alkylamine surfactant, wherein the glyphosate concentration is greater than 400 g/l based on glyphosate acid content.

2. A glyphosate concentrate according to claim 1, wherein the concentration of the potassium salt of glyphosate is greater than 400 g/l based on glyphosate acid, the total concentration of the alkylglycoside surfactant and alkoxylated alkylamine surfactant in the aqueous concentrate is from about 160 to 300 g/l and the ratio of alkylglycoside surfactant to alkoxylated alkylamine surfactant is from about 1 part by weight of alkylglycoside surfactant per 1 part by weight of alkoxylated alkylamine surfactant to about 5 parts by weight of alkylglycoside surfactant per 1 part by weight of alkoxylated alkylamine surfactant.

3. A glyphosate concentrate according to claim 1, wherein the glyphosate concentration is from 440 to 540 g/l based on glyphosate acid content.

4. A glyphosate concentrate according to claim 1, wherein the total content of the alkylglycoside surfactant and the alkoxylated alkylamine surfactant is from 160 to 300 g/l.

5. A glyphosate concentrate according to claim 4, wherein the ratio of alkylglycoside surfactant to alkoxylated alkylamine surfactant is from 1 part by weight of alkylglycoside surfactant per 1 part by weight of alkoxylated alkylamine surfactant to about 5 parts by weight of alkylglycoside surfactant per 1 part by weight of alkoxylated alkylamine surfactant.

6. A glyphosate concentrate according to claim 5, wherein the ratio of alkylglycoside surfactant to alkoxylated alkylamine surfactant is from 2 parts by weight of alkylglycoside surfactant per 1 part by weight of alkoxylated alkylamine surfactant to about 4 parts by weight of alkylglycoside surfactant per 1 part by weight of alkoxylated alkylamine surfactant.

7. A glyphosate concentrate according to claim 5, wherein the ratio of alkylglycoside surfactant to alkoxylated alkylamine surfactant is from 1.5 parts by weight of alkylglycoside surfactant per 1 part by weight of alkoxylated alkylamine surfactant to about 4 parts by weight of alkylglycoside surfactant per 1 part by weight of alkoxylated alkylamine surfactant.

8. The glyphosate concentrate of claim 4, wherein the total content of the alkylglycoside surfactant and the alkoxylated alkylamine surfactant is from 200 to 270 grams per liter.

9. A glyphosate concentrate according to claim 1, wherein the alkylglycoside surfactant has the formula

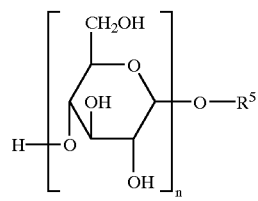

(I)

wherein n is the degree of polymerisation and is within the range from 1 to 3 and $R^5$ is a branched or straight chain alkyl group having from 4 to 18 carbon atoms or a mixture of alkyl groups having an average value of from 4 to 18 carbon atoms.

10. A glyphosate concentrate according to claim 9, wherein $R^5$ is 2-ethyl-1-hexyl, and n is from 1 to 2.

11. The glyphosate concentrate of claim 10, wherein n is from 1.5 to 1.9.

12. The glyphosate concentrate of claim 11, wherein n is about 1.75.

13. The glyphosate concentrate of claim 9, wherein n is an average of 1.7, and $R^5$ is a mixture of 45% octyl and 55% decyl.

14. The glyphosate concentrate of claim 9, wherein n is an average of 1.6, and $R^5$ is a mixture of 20% nonyl, 40% decyl and 40% undecyl.

15. A glyphosate concentrate according to claim 1, wherein the alkoxylated alkylamine surfactant is an ethoxylated or propoxylated or mixed ethoxylated and propoxylated C8 to C22 alkylamine having a degree of alkoxylation of from 1 to about 15.

16. A glyphosate concentrate according to claim 15 wherein the degree of alkoxylation is from 4 to 12.

17. The glyphosate concentrate of claim 15, wherein the alkoxylated alkylamine surfactant is an ethoxylated or propoxylated or mixed ethoxylated and propoxylated C10 to C20 alkylamine having a degree of alkoxylation of from 1 to about 15.

18. The glyphosate concentrate of claim 15, wherein the alkoxylated alkylamine surfactant is an alkoxylated derivative of cocoamine, an alkoxylated derivative of tallowamine, an alkoxylated derivative of oleylamine, an alkoxylated derivative of stearylamine, or a mixture thereof.

19. The glyphosate concentrate of claim 15, wherein the alkoxylated alkylamine surfactant is an ethoxylated C8 to C22 alkylamine having a degree of alkoxylation of from 1 to about 15.

20. The glyphosate concentrate of claim 19, wherein the alkoxylated alkylamine surfactant is an ethoxylated C10 to C20 alkylamine having a degree of alkoxylation of from 4 to 12.

21. The glyphosate concentrate of claim 20, wherein the alkoxylated alkylamine surfactant is an ethoxylated C10 to C20 alkylamine having a degree of alkoxylation of 5.

22. The glyphosate concentrate of claim 1, wherein the glyphosate concentration is from greater than 400 g/l to 550 g/l based on glyphosate acid content.

23. The glyphosate concentrate of claim 1, further comprising a viscosity modifying agent.

24. The glyphosate concentrate of claim 23, wherein the viscosity modifying agent is propylene glycol.

25. The glyphosate concentrate of claim 1, further comprising an antifoam agent.

26. A process of severely damaging or killing unwanted plants comprising preparing a diluted composition by diluting the glyphosate concentrate of claim 1 and applying to the plants a herbicidally effective amount of the diluted composition.

27. The process of claim 26, wherein the herbicidally effective amount of the diluted composition is from 0.001 to 20 kilograms per hectare.

28. The process of claim 27, wherein the herbicidally effective amount of the diluted composition is from 0.025 to 10 kilograms per hectare.

* * * * *